US012616588B2

(12) United States Patent
Kaufmann et al.

(10) Patent No.: US 12,616,588 B2
(45) Date of Patent: May 5, 2026

(54) SPINAL IMPLANT

(71) Applicant: GENESYS SPINE, Austin, TX (US)

(72) Inventors: Josh Kaufmann, Austin, TX (US); Greg Calbert, Austin, TX (US); Scott Bryant, Austin, TX (US); Derek Southard, Austin, TX (US); Landon Gilkey, Austin, TX (US); Matthew Philips, Dartmouth, MA (US)

(73) Assignee: GENESYS SPINE, Austin, TX (US)

( * ) Notice: Subject to any disclaimer, the term of this patent is extended or adjusted under 35 U.S.C. 154(b) by 0 days.

(21) Appl. No.: 18/884,169

(22) Filed: Sep. 13, 2024

(65) Prior Publication Data

US 2025/0090345 A1    Mar. 20, 2025

Related U.S. Application Data

(60) Provisional application No. 63/538,291, filed on Sep. 14, 2023.

(51) Int. Cl.
| | |
|---|---|
| *A61F 2/44* | (2006.01) |
| *A61F 2/46* | (2006.01) |
| *A61F 2/30* | (2006.01) |

(52) U.S. Cl.
CPC ............ *A61F 2/447* (2013.01); *A61F 2/4611* (2013.01); *A61F 2002/30535* (2013.01)

(58) Field of Classification Search
CPC ............ A61B 17/8033; A61B 17/8038; A61B 17/8042; A61B 17/8047; A61F 2/447; A61F 2/4455; A61F 2/446; A61F 2/4465
See application file for complete search history.

(56) References Cited

U.S. PATENT DOCUMENTS

| | | | |
|---|---|---|---|
| 5,304,179 | A | 4/1994 | Wagner |
| 6,156,037 | A | 12/2000 | LeHuec et al. |

(Continued)

FOREIGN PATENT DOCUMENTS

| | | |
|---|---|---|
| CN | 104546095 B | 5/2017 |
| CN | 105310805 B | 5/2017 |

(Continued)

OTHER PUBLICATIONS

Blackhawk TI Cervical Spacer System, "3D Printed Anterior Cervical Standalone Spacer System", downloaded from https://choicespine.com/blackhawk-ti/, downloaded on Aug. 27, 2023.

(Continued)

*Primary Examiner* — Jan Christopher L Merene
(74) *Attorney, Agent, or Firm* — Trop, Pruner & Hu, P.C.

(57) ABSTRACT

An embodiment includes an orthopedic fusion system comprising: a cage; a curved first channel coupling a lateral wall of the cage to a superior surface of the cage; a curved second channel coupling the lateral wall of the cage to an inferior surface of the cage; a third channel coupling the superior surface of the cage to the inferior surface of the cage; a curved first anchor configured to slide within the first channel; a curved second anchor configured to slide within the second channel; and a threaded projection extending outwardly from the lateral wall; a washer non-threadingly attached to the threaded projection; a cam non-threadingly attached to the threaded projection and directly contacting the washer; a nut threadingly attached to the threaded projection and directly contacting the cam.

20 Claims, 15 Drawing Sheets

(56) References Cited

U.S. PATENT DOCUMENTS

| | | | |
|---|---|---|---|
| 6,342,074 B1 | 1/2002 | Simpson | |
| 6,447,546 B1 | 9/2002 | Bramlet et al. | |
| 6,527,803 B1 | 3/2003 | Crozet et al. | |
| 7,004,944 B2 * | 2/2006 | Gause | A61B 17/8042 |
| | | | 606/294 |
| 7,235,101 B2 | 6/2007 | Berry et al. | |
| 7,563,284 B2 | 7/2009 | Coppes et al. | |
| 7,594,931 B2 | 9/2009 | Louis et al. | |
| 7,695,516 B2 | 4/2010 | Zeegers | |
| 7,704,279 B2 | 4/2010 | Moskowitz et al. | |
| 7,708,778 B2 | 5/2010 | Gordon et al. | |
| 7,993,375 B2 | 8/2011 | Bae et al. | |
| 8,147,556 B2 | 4/2012 | Louis et al. | |
| 8,172,885 B2 | 5/2012 | Songer et al. | |
| 8,313,528 B1 * | 11/2012 | Wensel | A61F 2/447 |
| | | | 623/17.11 |
| 8,328,872 B2 | 12/2012 | Duffield et al. | |
| 8,343,219 B2 | 1/2013 | Allain et al. | |
| RE43,998 E | 2/2013 | Aoki et al. | |
| 8,460,385 B1 | 6/2013 | Wensel | |
| 8,523,945 B1 * | 9/2013 | Wensel | A61B 17/70 |
| | | | 623/17.11 |
| 8,641,768 B2 | 2/2014 | Duffield et al. | |
| 8,778,001 B2 | 7/2014 | Thramann et al. | |
| 8,778,025 B2 | 7/2014 | Ragab et al. | |
| D712,036 S | 8/2014 | Davenport | |
| 8,808,304 B2 | 8/2014 | Weiman et al. | |
| 8,814,911 B2 | 8/2014 | Jackson | |
| 8,852,193 B2 | 10/2014 | Hushka et al. | |
| 8,882,840 B2 | 11/2014 | McClintock et al. | |
| 8,888,817 B2 | 11/2014 | Sherman et al. | |
| 8,932,359 B2 | 1/2015 | Brett | |
| 9,017,412 B2 | 4/2015 | Wolters et al. | |
| 9,039,774 B2 | 5/2015 | Chataigner et al. | |
| 9,044,337 B2 | 6/2015 | Dinville et al. | |
| 9,060,808 B2 | 6/2015 | Overes et al. | |
| 9,078,765 B2 | 7/2015 | Louis et al. | |
| 9,101,493 B2 | 8/2015 | Trudeau et al. | |
| 9,173,745 B2 | 11/2015 | Dinville et al. | |
| 9,173,750 B2 | 11/2015 | Weiman et al. | |
| 9,226,832 B2 | 1/2016 | Lambrecht et al. | |
| 9,241,738 B2 | 1/2016 | Quevedo et al. | |
| 9,241,806 B2 * | 1/2016 | Suh | A61B 17/8625 |
| 9,333,095 B2 | 5/2016 | Beaurain et al. | |
| 9,364,343 B2 | 6/2016 | Duffield et al. | |
| 9,387,087 B2 | 7/2016 | Tyber | |
| 9,402,738 B2 | 8/2016 | Niemiec et al. | |
| 9,468,534 B2 | 10/2016 | Garber et al. | |
| 9,517,144 B2 | 12/2016 | McAtamney et al. | |
| 9,585,765 B2 | 3/2017 | Niemiec et al. | |
| 9,592,131 B2 | 3/2017 | Sandstrom et al. | |
| 9,649,199 B2 | 5/2017 | Louis et al. | |
| 9,675,388 B2 | 6/2017 | Boyer, II et al. | |
| 9,693,871 B2 | 7/2017 | Richerme et al. | |
| 9,763,803 B2 | 9/2017 | Dinville et al. | |
| 9,775,722 B2 | 10/2017 | Kim et al. | |
| 9,795,485 B2 | 10/2017 | Allain et al. | |
| 9,801,733 B2 | 10/2017 | Wolters et al. | |
| 9,833,331 B2 | 12/2017 | Dinville et al. | |
| 10,080,667 B2 | 9/2018 | Trudeau et al. | |
| 10,098,755 B2 | 10/2018 | Kaufmann et al. | |
| 10,159,584 B2 | 12/2018 | Carnes et al. | |
| 10,245,157 B2 | 4/2019 | Chataigner et al. | |
| 10,258,479 B2 | 4/2019 | Stewart et al. | |
| 10,292,833 B2 | 5/2019 | Sicotte et al. | |
| 10,485,591 B2 | 11/2019 | Lequette et al. | |
| 10,507,119 B2 | 12/2019 | Laubert et al. | |
| 10,512,547 B2 | 12/2019 | Altarac et al. | |
| 10,548,743 B2 | 2/2020 | Faulhaber | |
| 10,631,999 B2 | 4/2020 | Gilbride et al. | |
| 10,729,556 B2 | 8/2020 | Capote et al. | |
| 10,751,187 B2 | 8/2020 | Allain et al. | |
| 10,806,592 B2 | 10/2020 | Donner et al. | |
| 10,925,750 B2 | 2/2021 | Zappacosta et al. | |
| 10,980,641 B2 | 4/2021 | Altarac et al. | |
| 11,007,066 B2 | 5/2021 | Kaufmann et al. | |
| 11,116,645 B2 | 9/2021 | Zakelj | |
| 11,135,069 B2 | 10/2021 | Eisen et al. | |
| 11,173,042 B2 | 11/2021 | Walsh et al. | |
| 11,179,246 B2 | 11/2021 | Seifert et al. | |
| 11,191,647 B2 | 12/2021 | Ashley et al. | |
| 11,213,328 B2 | 1/2022 | Lauf et al. | |
| 11,273,049 B2 | 3/2022 | Bennett et al. | |
| 11,419,735 B2 | 8/2022 | Barreiro et al. | |
| 11,633,290 B2 | 4/2023 | Valkoun et al. | |
| 11,672,674 B2 | 6/2023 | Shoshtaev et al. | |
| 11,678,996 B2 | 6/2023 | Gamache et al. | |
| 11,684,483 B2 | 6/2023 | Gilbride et al. | |
| 11,728,339 B2 | 8/2023 | Flickinger et al. | |
| 11,911,288 B2 | 2/2024 | Kaufmann et al. | |
| 2006/0293668 A1 * | 12/2006 | May | A61B 17/8047 |
| | | | 606/86 A |
| 2010/0204739 A1 | 8/2010 | Bae et al. | |
| 2010/0312345 A1 * | 12/2010 | Duffield | A61F 2/4455 |
| | | | 623/17.16 |
| 2011/0196494 A1 | 8/2011 | Yedlicka et al. | |
| 2011/0230971 A1 * | 9/2011 | Donner | A61B 17/846 |
| | | | 606/246 |
| 2012/0116466 A1 | 5/2012 | Dinville et al. | |
| 2012/0130496 A1 | 5/2012 | Duffield et al. | |
| 2012/0130497 A1 | 5/2012 | Taylor | |
| 2012/0191196 A1 | 7/2012 | Louis et al. | |
| 2012/0277870 A1 | 11/2012 | Wolters et al. | |
| 2013/0060339 A1 | 3/2013 | Duffield et al. | |
| 2013/0073044 A1 * | 3/2013 | Gamache | A61B 17/8042 |
| | | | 623/17.16 |
| 2013/0150968 A1 | 6/2013 | Dinville et al. | |
| 2013/0190874 A1 * | 7/2013 | Glazer | A61F 2/447 |
| | | | 623/17.11 |
| 2013/0226300 A1 | 8/2013 | Chataigner et al. | |
| 2013/0345813 A1 | 12/2013 | Frank et al. | |
| 2014/0012384 A1 * | 1/2014 | Kana | A61F 2/30744 |
| | | | 623/17.16 |
| 2015/0045893 A1 | 2/2015 | Dinville et al. | |
| 2015/0051702 A1 | 2/2015 | Chataigner et al. | |
| 2015/0051704 A1 | 2/2015 | Duffield et al. | |
| 2015/0127107 A1 | 5/2015 | Kim et al. | |
| 2015/0209089 A1 | 7/2015 | Chataigner et al. | |
| 2015/0250605 A1 | 9/2015 | Chataigner et al. | |
| 2015/0305887 A1 | 10/2015 | McAtamney et al. | |
| 2015/0320568 A1 | 11/2015 | Ameil et al. | |
| 2016/0051380 A1 | 2/2016 | Dinville et al. | |
| 2016/0100953 A1 | 4/2016 | Dinville et al. | |
| 2016/0242930 A1 | 8/2016 | Duffield et al. | |
| 2016/0324652 A1 | 11/2016 | Brow | |
| 2017/0042692 A1 | 2/2017 | Stewart et al. | |
| 2017/0056198 A1 | 3/2017 | Ameil et al. | |
| 2017/0135822 A1 | 5/2017 | Bender et al. | |
| 2017/0156760 A1 | 6/2017 | Abrahams et al. | |
| 2017/0246007 A1 | 8/2017 | Chataigner et al. | |
| 2017/0246008 A1 | 8/2017 | Mercier et al. | |
| 2017/0311997 A1 | 11/2017 | Lequette et al. | |
| 2017/0319354 A1 | 11/2017 | Louis et al. | |
| 2018/0235771 A1 | 8/2018 | Chataigner et al. | |
| 2018/0318100 A1 * | 11/2018 | Altarac | A61F 2/4455 |
| 2020/0138595 A1 * | 5/2020 | Shoshtaev | A61F 2/4611 |
| 2021/0085483 A1 * | 3/2021 | MacMillan | A61F 2/4611 |
| 2022/0362033 A1 | 11/2022 | Hansell et al. | |
| 2024/0299182 A1 | 9/2024 | Kaufmann et al. | |

FOREIGN PATENT DOCUMENTS

| | | |
|---|---|---|
| CN | 112618117 A | 4/2021 |
| CN | 113855343 B | 11/2022 |
| WO | 010121028 A2 | 10/2010 |
| WO | 2023144475 A1 | 8/2023 |

OTHER PUBLICATIONS

Orthopedic Design & Technology, "FDA OKs 4WEB's Cervical Stand-Alone Interbody Fusion Device", dated Aug. 29, 2019, downloaded from https://www.odtmag.com/contents/view_breaking-news/

(56)                    References Cited

OTHER PUBLICATIONS 2019-08-29/fda-oks-4webs-cervical-stand-alone-interbody-fusion-device/.

Orthopedic Design & Technology, "DePuy Synthes Spine Launches Two New Devices at NASS" dated Oct. 27, 2016, downloaded from https://www.odtmag.com/contents/view_breaking-news/2016-10-27/depuy-synthes-spine-launches- two-new-devices-at-nass/.

ZimVie Inc., "Optio-C Anterior Cervical System", downloaded from https://www.zimvie.com/en/spine/cervical-solutions/optio-c--anterior-cervical-system.html, downloaded on Aug. 27, 2023.

Orthopedic Design & Technology, "Zavation cervical spine—Varisync", dated Aug. 19, 2022, https://www.odtmag.com/contents/view_breaking-news/2022-08-19/zavations-cervical-intervertebral-body-fusion-device-cleared-by-fda/.

Double Medical, "Zero-Profile Anterior Cervical Intervertebral Locking Plate and Cage Combination System", downloaded from https://www.doublemedicalgp.com/zero-profile-anterior-cervical-intervertebral-locking-plate-and-cage-combination-system_p49.html, downloaded on Aug. 27, 2023.

Orthopedics This Week, RRY Publications, "Stand-Alone Cervical System Updated With Turn Lock", dated Sep. 24, 2020, downloaded from https://ryortho.com/breaking/stand-alone-cervical-system-updated-with-turn-lock/.

Medical Device Network, "ChoiceSpine launches next-generation interbody fusion system", dated Apr. 20, 2022, downloaded from https://www.medicaldevice-network.com/news/choicespine-launch-interbody-fusion-system/.

Spinal Elements, "Cervical interbody fusion cage Ceres®-C", downloaded from https://www.medicalexpo.com/prod/spinal-elements/product-119640-835061.html, downloaded on Aug. 27, 2023.

Canadian Patent Office, Examiner's Report mailed Mar. 31, 2023 in Canadian Patent Application No. 3024894 (1 Page).

Canadian Patent Office, Examiner's Report mailed Oct. 17, 2022 in Canadian Patent Application No. 3024894 (4 pages).

European Patent Office, Supplemental European Search Report mailed Jan. 3, 2020 in European Patent Application No. 178035820 (7 pages).

European Patent Office, Communication under Rule 71(3) EPC dated Jun. 20, 2023 in European Patent Application No. 178035820 (57 pages).

The International Searching Authority, Notification of Transmittal of the International Search Report and Written Opinion, mailed Sep. 4, 2017 in International Application No. PCT/US2017/034471 (11 pages).

* cited by examiner

112

111

110

142

141

SPINAL IMPLANT

PRIORITY CLAIM

This application claims priority to U.S. Provisional Patent Application No. 63/538,291, filed on Sep. 14, 2023, and entitled "Spinal Implant", the content of which is hereby incorporated by reference.

TECHNICAL FIELD

Embodiments of the invention are in the field of orthopedic implants.

BACKGROUND

As addressed in U.S. Pat. No. 10,098,755, fixation devices can be used to provide, for example, immobilization and stabilization of spinal segments in patients (e.g., humans, dogs, cats, and other animals). Fixation devices may be used to help fuse bone segments (e.g., vertebrae) in the treatment of instabilities or deformities of, for example, the cervical, thoracic, lumbar, and/or sacral spine. Such instabilities or deformities may include, for example, degenerative disc disease (DDD); spondylolisthesis; trauma (i.e., fracture or dislocation); spinal stenosis; curvatures (i.e., scoliosis, kyphosis, and/or lordosis); tumor; pseudoarthrosis; and failed previous fusions.

One such fixation device may include an interbody spacer implanted using techniques such as Anterior Lumbar Interbody Fusion (ALIF), Posterior Lumbar Interbody Fusion (PLIF), or Transforaminal Lumbar Interbody Fusion (TLIF) surgical techniques. The spacers used in these techniques are placed in the interdiscal space between adjacent vertebrae of the spine. Many times an exterior plate is used in conjunction with the spacer to hold the adjacent vertebrae while the fusion occurs.

Ideally, the spacer should stabilize the intervertebral space and allow fusion of the adjacent vertebrae. Moreover, during the time it takes for fusion to occur, the interbody spacer should have sufficient structural integrity to withstand the stress of maintaining the space without substantially degrading or deforming and have sufficient stability to remain securely in place prior to actual bone ingrowth fusion.

The degree or success of union, loads produced by weight bearing, and activity levels will, among other conditions, dictate the longevity of the implant. Robust fixation systems are needed to lessen risks associated with fixation and to promote better outcomes for patients.

BRIEF DESCRIPTION OF THE DRAWINGS

Features and advantages of embodiments of the present invention will become apparent from the appended claims, the following detailed description of one or more example embodiments, and the corresponding figures, in which:

DETAILED DESCRIPTION

Figure 1A:
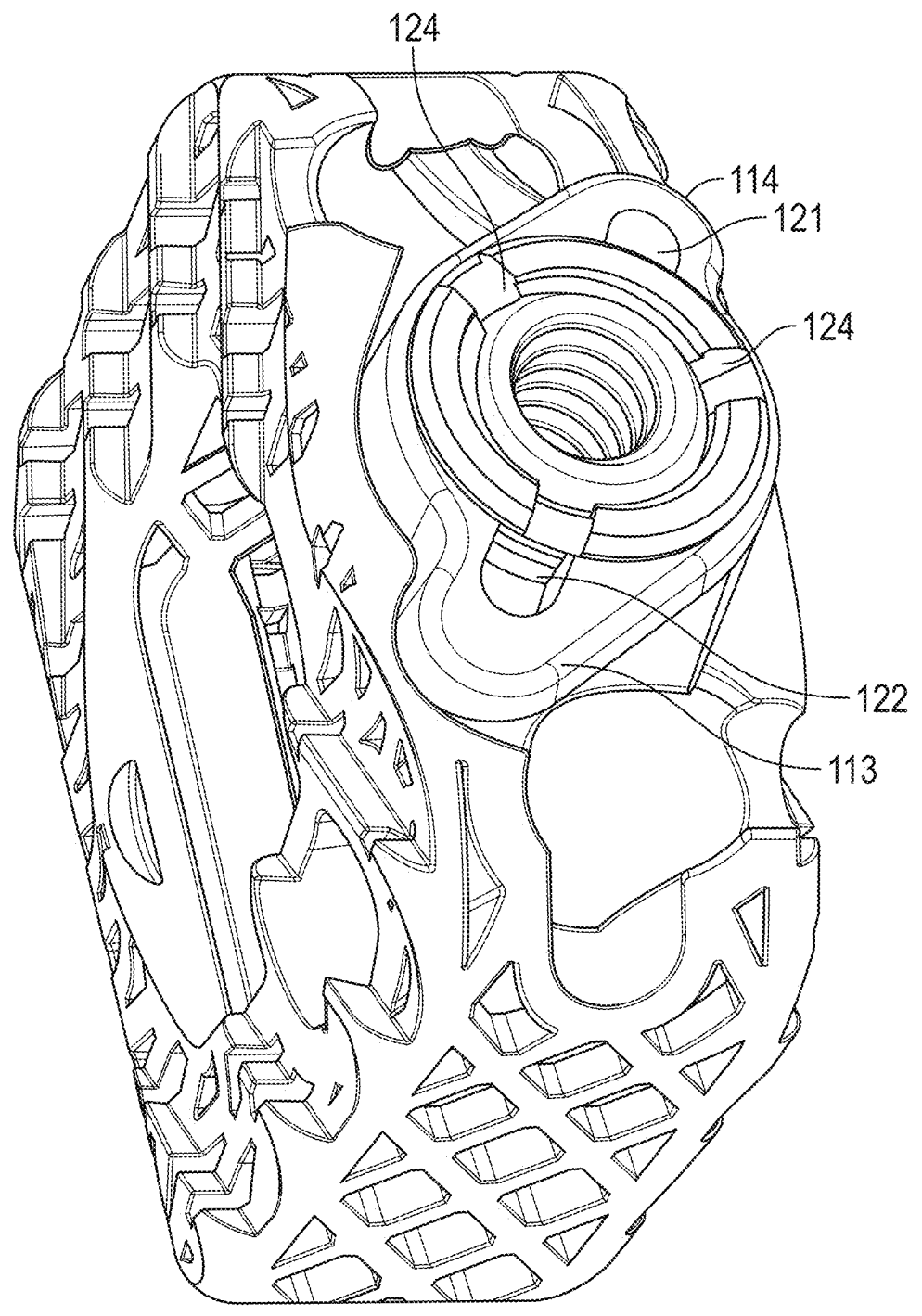
FIG. 1A includes a perspective view of an embodiment of a standalone interbody cage with a cam in an open position or configuration.
Figure 1B:
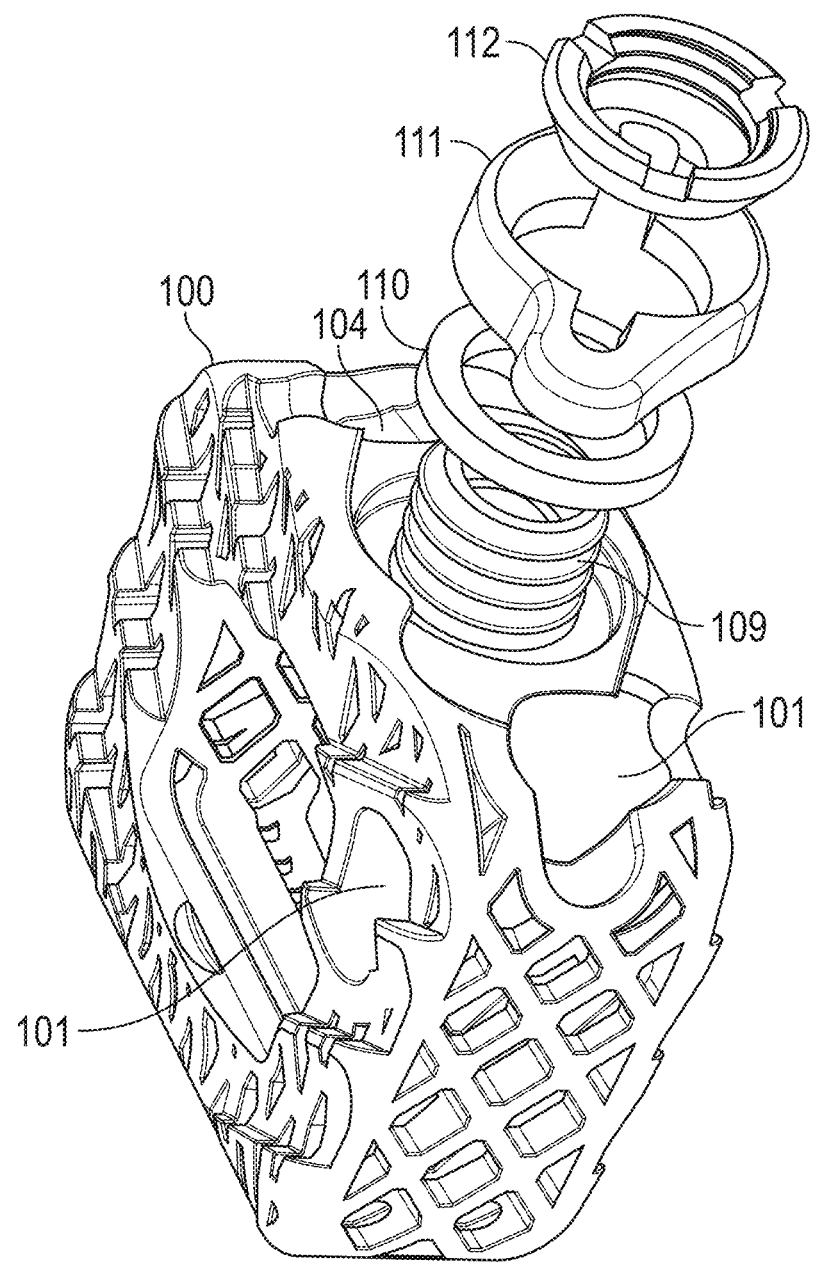
FIG. 1B includes an assembly drawing of the embodiment of FIG. 1A.

In the following description, numerous specific details are set forth. However, it is understood that embodiments of the invention may be practiced without these specific details. Well-known structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" and the like describe a common object and indicate that different instances of like objects are being referred to. Such adjectives are not intended to imply the objects so described must be in a given sequence, either temporally, spatially, in ranking, or in any other manner. Also, the terms "coupled" and "connected," along with their derivatives, may be used. In particular embodiments, "connected" may be used to indicate that two or more elements are in direct physical contact with each other and "coupled" may mean that two or more elements co-operate or interact with each other, but they may or may not be in direct physical contact.

An embodiment includes a cam that locks bone anchors in place. An embodiment includes an orthopedic fusion system comprising a cage (100), a curved first channel (101) coupling a lateral wall (102) of the cage to a superior surface (103) of the cage, and a curved second channel (104) coupling the lateral wall of the cage to an inferior surface (105) of the cage. The embodiment further includes a third channel (106) coupling the superior surface of the cage to the inferior surface of the cage, a curved first anchor (107) configured to slide within the first channel, and a curved second anchor (108) configured to slide within the second channel. A threaded projection (109) extends outwardly from the lateral wall. A washer (110) non-threadingly attaches to the threaded projection. A cam (111) non-threadingly attaches to the threaded projection and directly contacts the washer. A nut (112) threadingly attaches to the threaded projection and directly contacting the cam. For example, a tool with projections may insert into voids 124 to tighten nut 112 onto post 109. Post 109 may or may not be monolithic with surfaces/walls 102, 103, 105.

The washer is formed of polyetheretherketone (PEEK) in an embodiment. A tuning fork looking device (e.g., device with two projections to interface two apertures (121, 122) on the cam) twists cam 114 piece from open (which you need when driving two anchors into vertebral plates via the cage—see, e.g., FIG. 1A) to closed (after the anchors are implanted—see, e.g., FIG. 1C). The closed position keeps the anchors from backing out of the vertebral plates over time. The nut 112 keeps the cam 111 and washer 110 pieces on threaded neck 109. The cam stays open or shut based on resistance imposed on the cam by the washer.

As used herein, a "cam" is a rotating or sliding piece (such as an eccentric wheel or a cylinder with an irregular shape) in a mechanical linkage.

In an embodiment the cam includes: a first arm (113) that projects across a portion of the first channel in a first orientation of the cam with respect to the cage; and a second arm (114) that projects across a portion of the second channel in the first orientation. See, for example, FIG. 1C or 1D.

In an embodiment, in a second orientation of the cam with respect to the cage: (a) the first arm does not project across the portion of the first channel; and (b) the second arm does not project across the portion of the second channel in the second orientation. The cam is rotationally linked to the threaded projection and is configured to rotate between the first and second orientations. See, for example, FIG. 1A.

In an embodiment in the first orientation a portion of the first arm is lateral to a proximal end (115) of the first anchor and prevents the first anchor from backing out of the first channel. A vertical plane (116) in the first orientation the first anchor is completely surrounded by an interior wall of the first channel.

In an embodiment the first anchor includes a projection (117) configured to abut a wall (118) of the first channel to prevent a proximal portion of the first anchor from passing through the first channel.

In an embodiment the orthopedic fusion system comprises an insertion tool, the insertion tool comprising: a first insertion tool arm (141) configured to travel along a first arcuate path to drive the first anchor along the first channel; and a second insertion tool arm (142) configured to travel along a second arcuate path to drive the second anchor along the second channel. See, for example, FIGS. 2A-2D. In an embodiment, the first and second insertion tool arms are configured to respectively travel along the first and second arcuate paths simultaneously with one another. As a result, the first and second anchors are configured to deploy into the first and second channels simultaneously with one another.

An embodiment includes a withdrawal tool, the withdrawal tool comprising a first withdrawal tool arm configured to travel along an additional first arcuate path to withdraw the first anchor from the first channel.

An embodiment comprising a fourth channel 123 coupling the lateral wall of the cage to third channel 106. For example, element 109 may be hollow and allow a surgeon to visually and/or physically access channel 106 via channel 123.

Figure 1C:
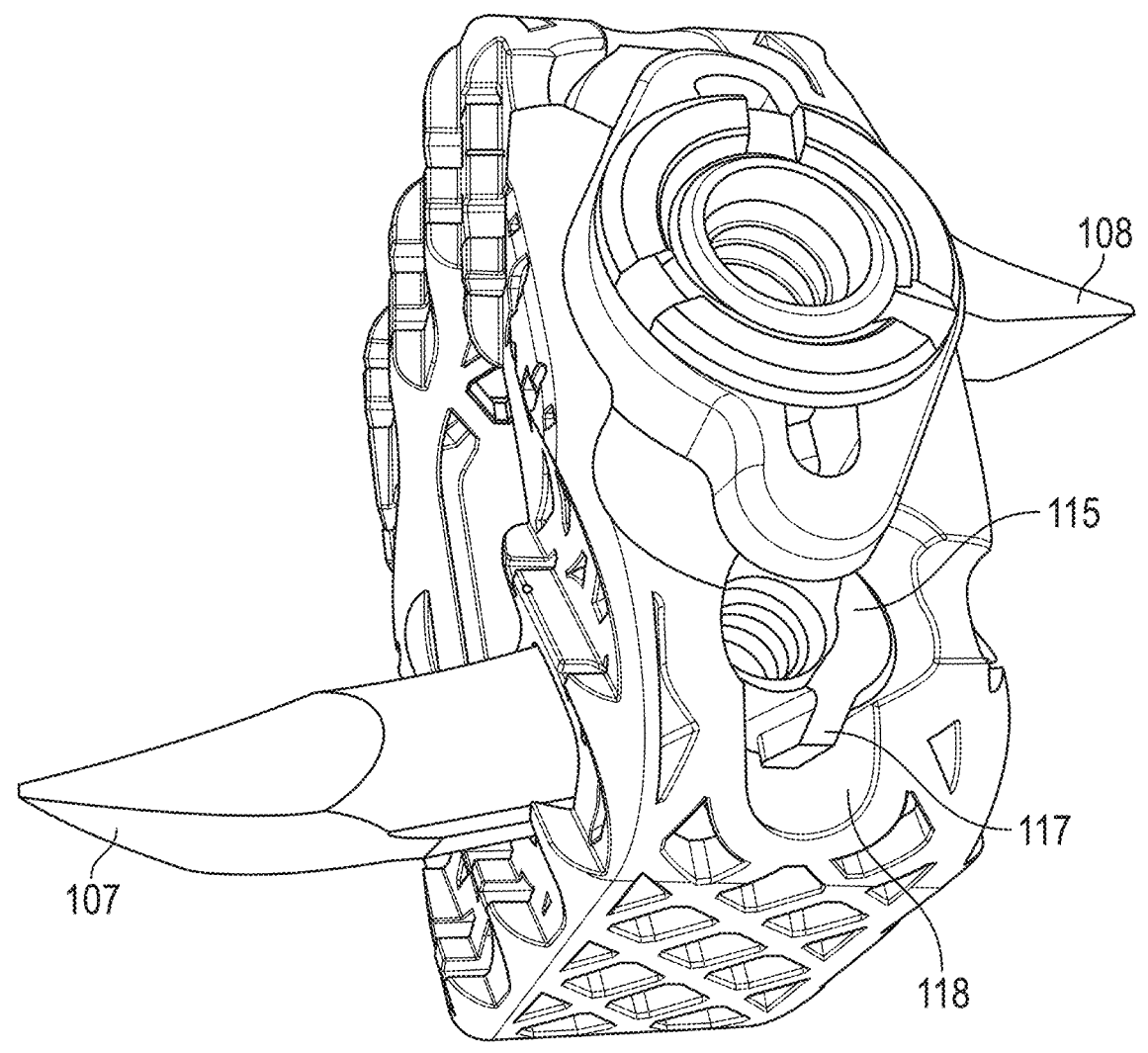
FIG. 1C includes an perspective view of the embodiment of FIG. 1A including anchors with the cam in a closed position or configuration.
Figure 1D:
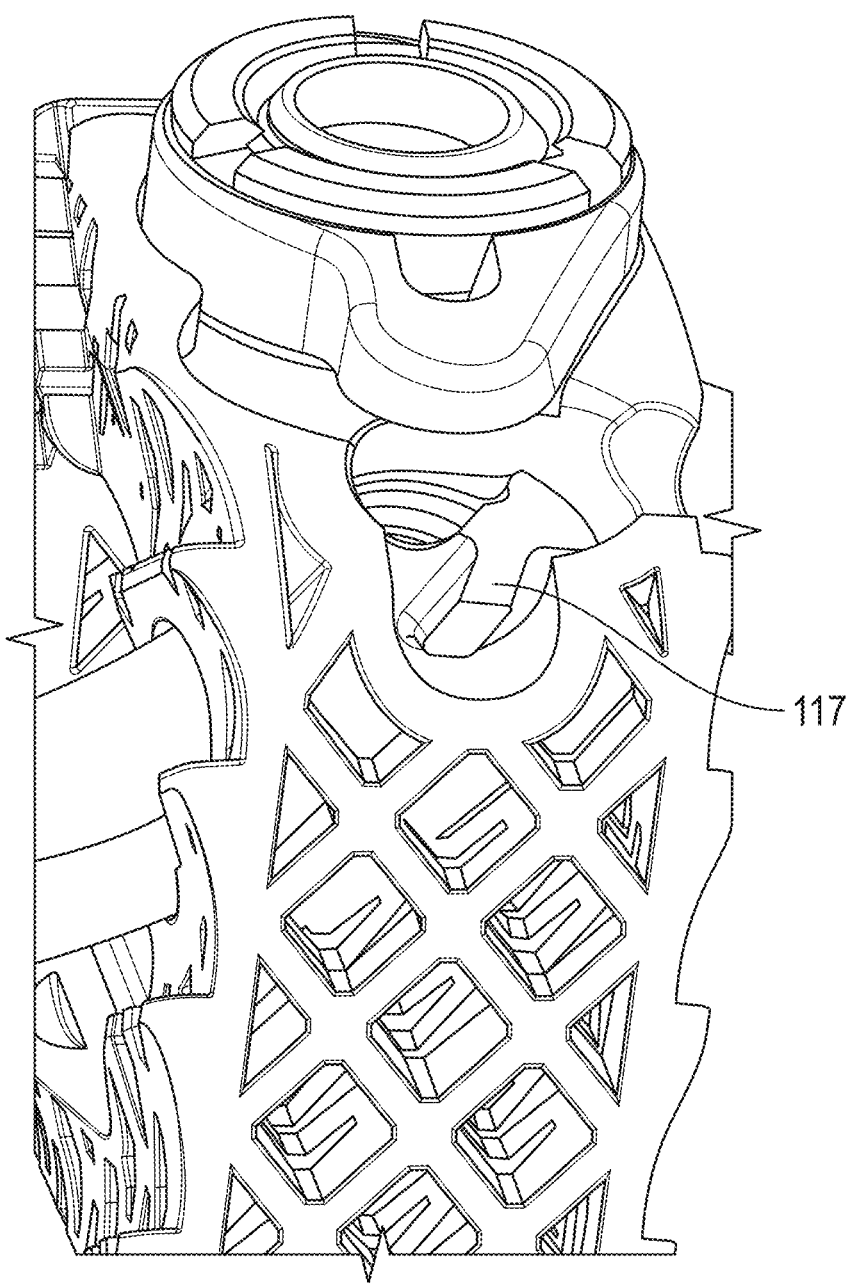
FIG. 1D includes an perspective view of the embodiment of FIG. 1A including anchors with the cam in a closed position or configuration.

In an embodiment an additional channel may be located between the first and second channels and an additional anchor may configured to slide within the additional channel. For example, the embodiment of FIG. 1A is configured for two anchors but other embodiments may include additional channels and anchors. For instance, an embodiment may include two channels and anchors to deploy through surface 103 and two channels and anchors to deploy through surface 105. Other embodiments may include fewer channels (e.g., 1) or more channels (e.g., 3, 4, or more) for anchors. For example, while a cervical implant may have less "real estate" for such channels a lumbar implant may allow for, as an example, two channels for superior facing anchors and two channels for inferior facing anchors.

In an embodiment a linear axis (119) intersects the lateral wall and the first and second channels.

In an embodiment the first anchor includes an arcuate outer wall (120) defining an arc (e.g., see element 152 of FIG. 2D) that extends along a majority of an overall length of the first anchor. In an embodiment the arc has a single consistent radius of curvature.

In an embodiment the cam is non-fixedly coupled to the washer and is rotationally coupled to the washer. The nut is tightened against the cam with a predetermined level of force to force the cam against the washer. This level of force can be achieved via threading on element 109 and tolerances for elements 110, 111, 112.

As compared to U.S. Pat. No. 11,007,066, the above embodiments may provide an easier assembly process of the cage considering the washer, cam, and nut may be necessarily small for cervical cages and the like. Further, the use of the cam may provide an alternative user experience preferable to users who prefer to rotate the cam into the first orientation to lock the anchors into their deployed state.

In an embodiment the anchors include a guide on a side wall of the anchor that mates with a channel in the cage (or vice versa in some embodiments). Anchors may include teeth or other gripping members to grip bone or tissue upon implantation. The cage body (which may include PEEK) may include apertures that retain radiopaque metal members to allow for imaging of such metal members. For example, Tantalum pins may be used to aid visualization of a transparent PEEK body. In an embodiment portions of the body 110 may be coated with a material, such as titanium to promote tissue ingrowth.

Figure 1E:
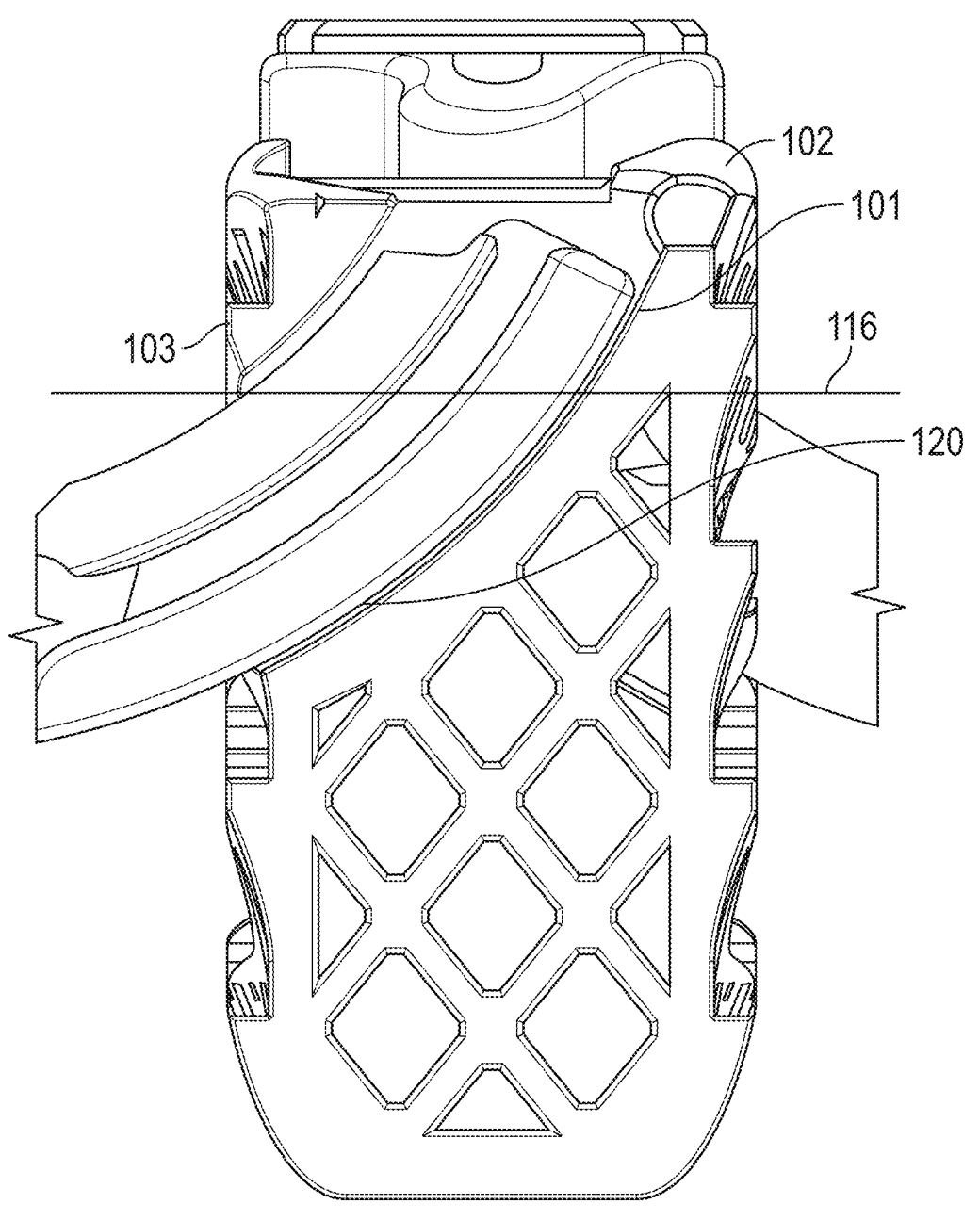
FIG. 1E includes a cross-sectional view of the embodiment of FIG. 1A including anchors with the cam in a closed position or configuration.
Figure 1F:
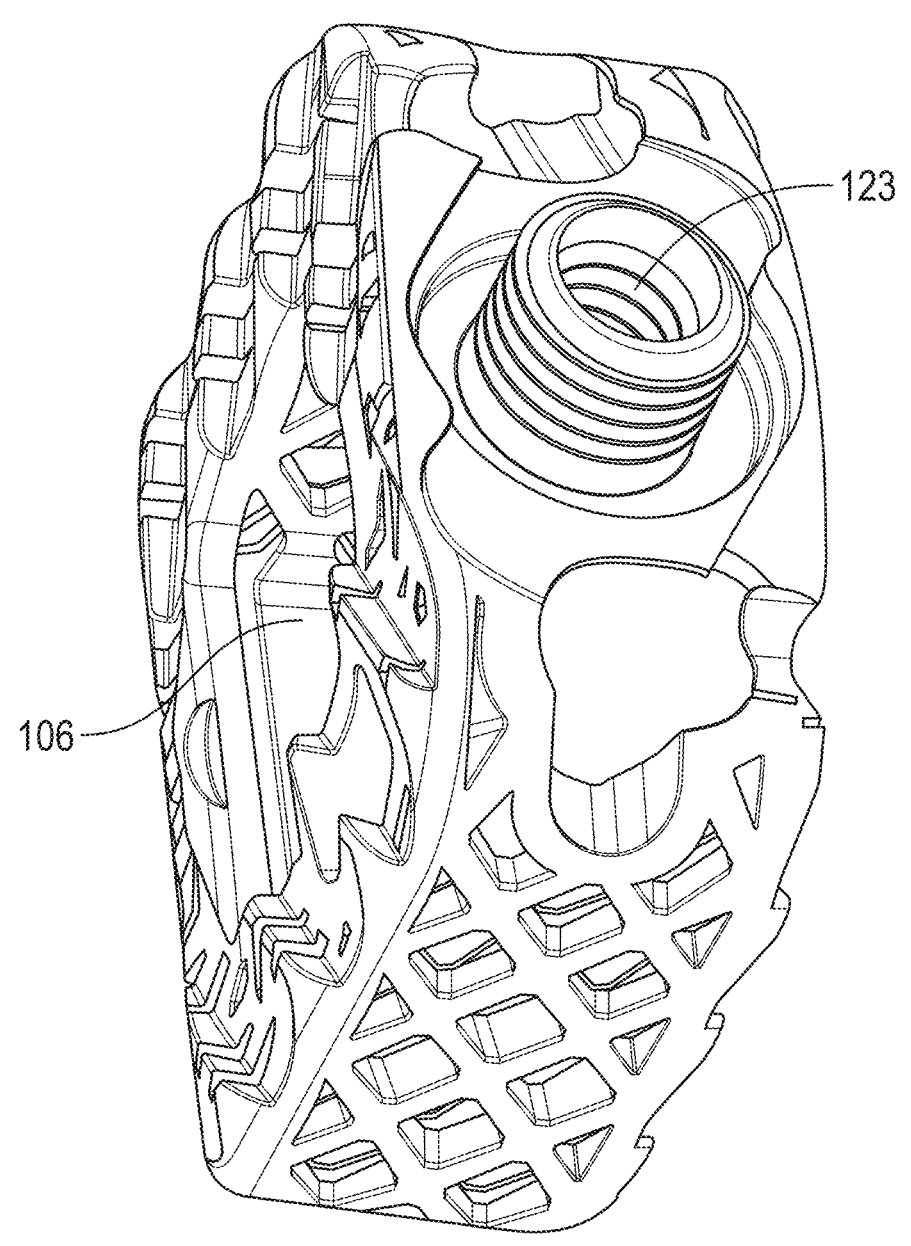
FIG. 1F includes an perspective view of the cage of the embodiment of FIG. 1A.
Figure 1G:
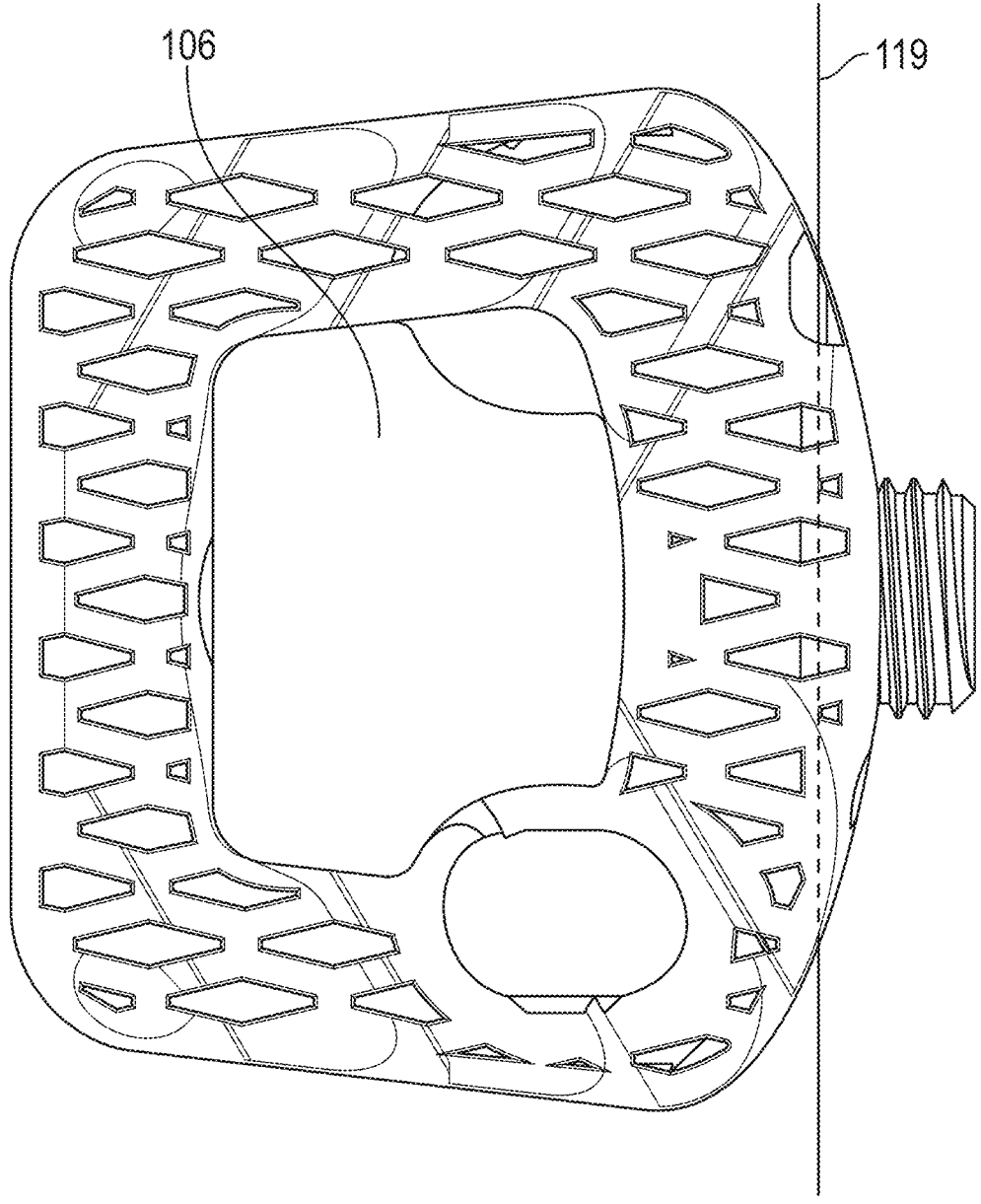
FIG. 1G includes a top view of the cage of the embodiment of FIG. 1A.
Figure 1H:
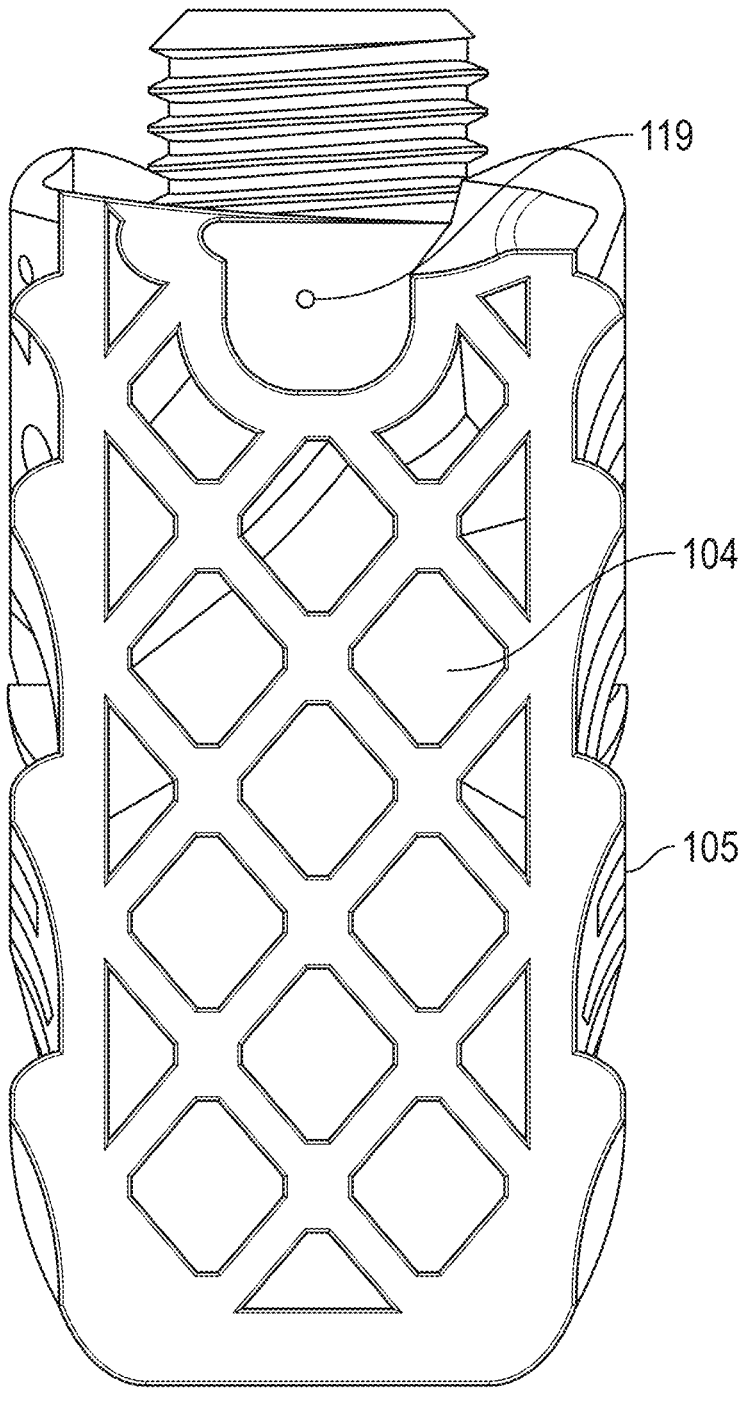
FIG. 1H includes a side view of the cage of the embodiment of FIG. 1A.
Figure 1I:
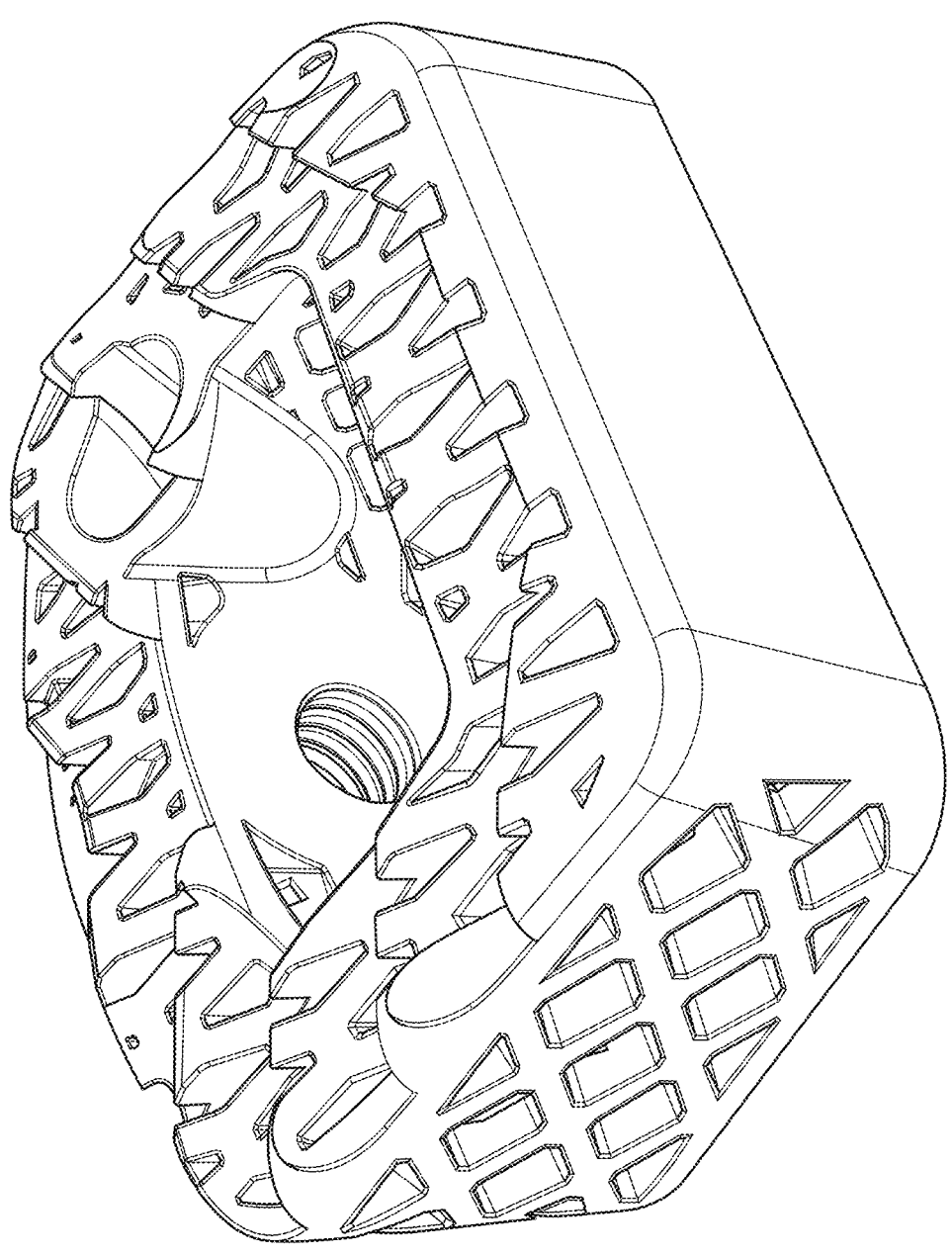
FIG. 1I includes a perspective view of the cage of the embodiment of FIG. 1A.
Figure 2A:
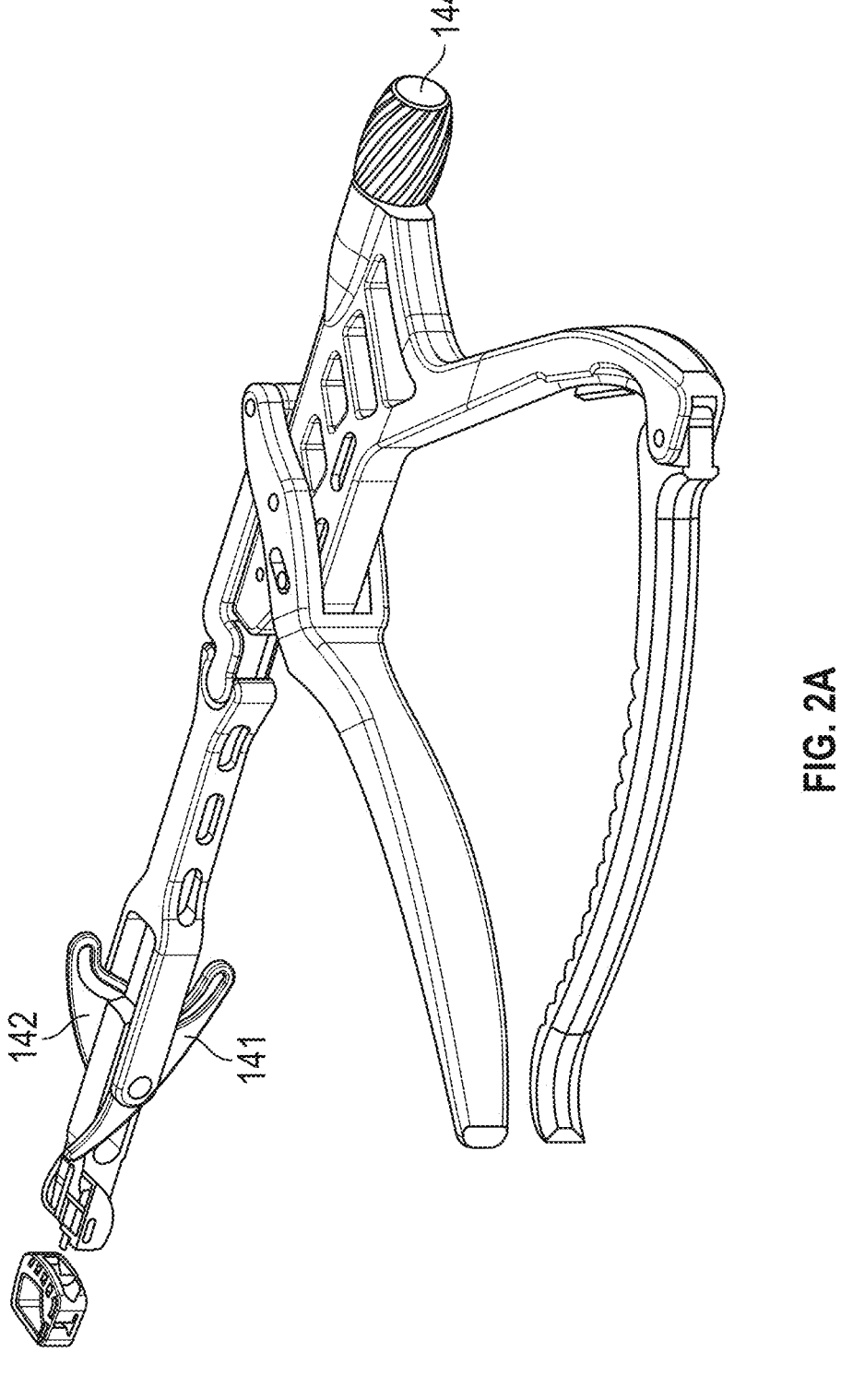
FIG. 2A includes a perspective view of an embodiment of a standalone interbody cage, anchors, and insertion tool.
Figure 2B:
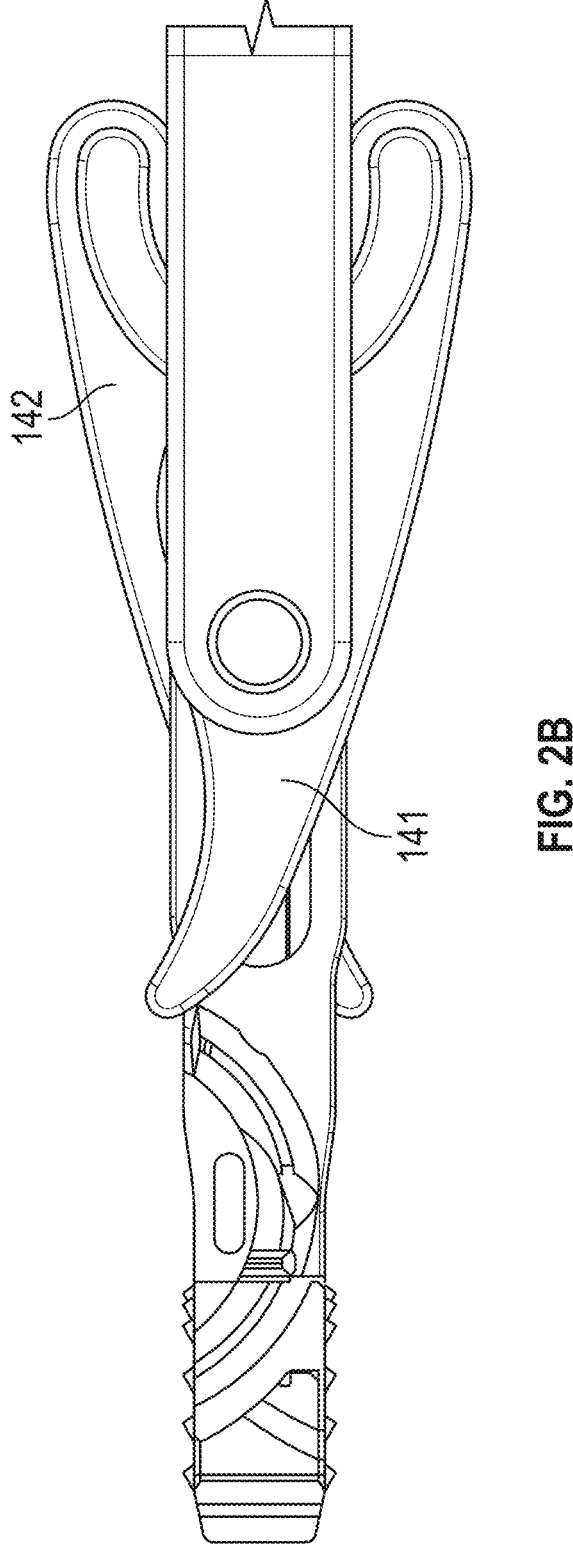
FIGS. 2B, 2C, 2D include cross-sectional views of an embodiment of a standalone interbody cage, anchors, and insertion tool at various points of anchor deployment within a channel of the cage.
Figure 2C:
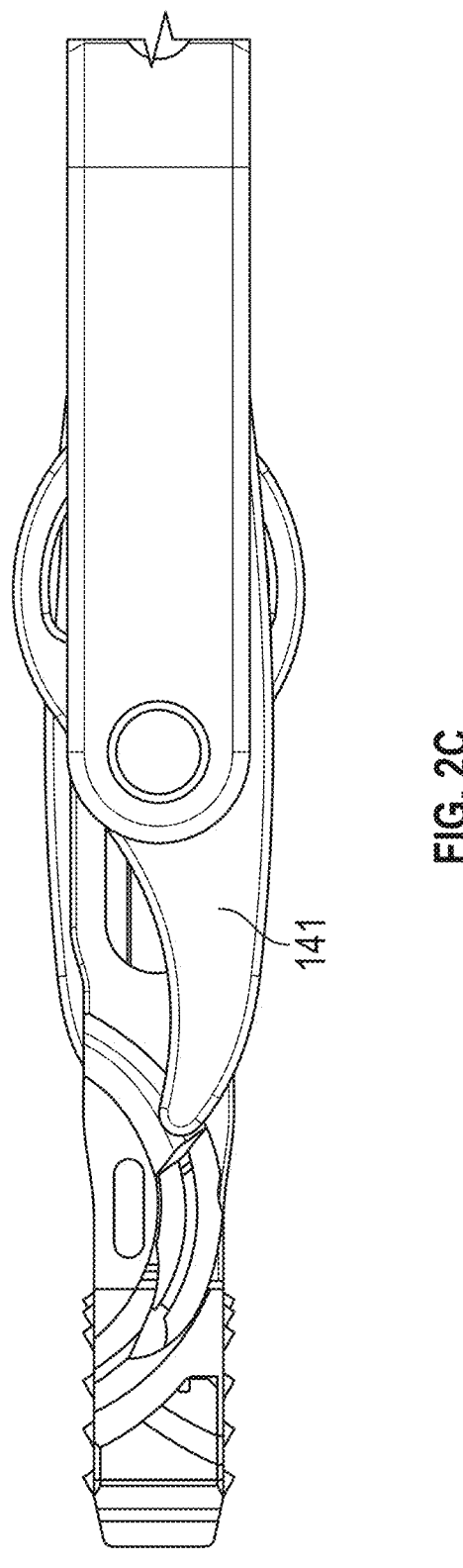
Figure 2D:
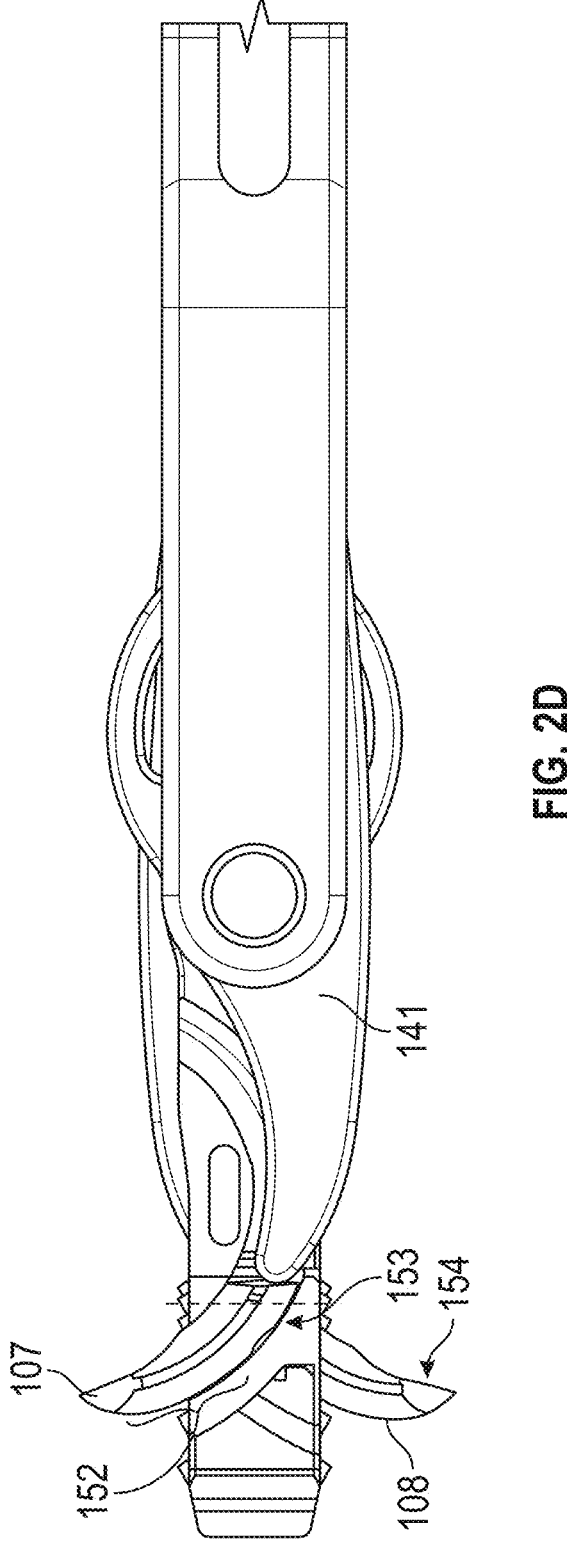

The main cage body may have ramps or angled portions (see, e.g., element 153 of FIG. 2D) that help project anchors in superior and inferior directions respectively to deploy into bone portions located superior and inferior to the spacer. In an embodiment the anchors are curved (see FIG. 1E). The curved nature of the anchors allows for a more vertical implantation into bone. For example, a flattened anchor portion 154 is generally vertical in FIG. 2D illustrating an insertion path that generally has more than 45 degrees of rotation. For example, from insertion (FIG. 2B) to final implantation (FIG. 1E) the tip of the anchor may rotate 45, 55, 65, 75, 85 degrees or more. This results in better purchase with the vertebrae. For example, in FIG. 2B the distal tip of anchor 111 is generally horizontal and in FIG. 1E is generally vertical constituting almost a 90 degree rotation. This cases implantation for the physician while still provide for secure bone purchase.

FIGS. 2A-2D depict an insertion tool for the anchors. The insertion tool allows for simultaneous insertion of anchors into bone. The anchors 107, 108 may deploy simultaneously in superior and inferior directions. By "simultaneous" what is meant is that at some point in time both anchors are being deployed (e.g., FIG. 2D). Simultaneous does not necessarily require that each anchor move in lock step with each other but in some embodiments that is indeed the case. However, in other embodiments the anchors may be deployed independently/non-simultaneously of each other (e.g., one deployed and then another deployed). For example, the same tool shown in FIG. 2A may be deployed with only a single anchor and is so doing only a single anchor is deployed regardless of arms 141, 142 both articulating simultaneously. Another embodiment of tool 140 may include only a single arm that still advances along an arcuate path to project a single anchor along a superior or inferior arcuate path.

Tool 140 may be rotated via knob 144 (FIG. 2A) to couple the insertion tool to cage member 109 via the internal threads of element 109.

As shown in FIG. 2D, one anchor projects upwards and another anchor projects downwards. The anchors are not vertically aligned but are present in the same horizontal plane (e.g., a plane that intersects both channels), a plane that aligns with the main axis of the spacer. The anchors are equally offset from the vertical axis (e.g., a vertical axis that bisects the orifice 106). Due to this offset, multiple instances of the body may be employed in a multi-level fusion. In such a case, a first body may be inserted into disc space above a vertebra and a second body may be inserted into disc space below that same vertebra. Due to the offset of the anchors, even if the bodies are aligned vertically, the upward projecting anchor of the lower second body will not interfere with a downward projecting anchor of the upper first body. Embodiments include a set of multiple cages for a multilevel fusion as described above. Further, due to the offset between anchors each of the anchor channels may traverse more than 50% of the height of the body (e.g., start in the bottom half of the cage and traverse through the top half of the cage). If the body is configured for cervical fusion, the body is necessarily quite small (e.g., as opposed to lumbar bodies) and therefore "real estate" is limited. However, staggering of the anchors allows for longer and thicker anchors that have greater strength to accommodate both insertion but also post-operative loading.

An embodiment includes a set of anchors that come in varying lengths, any of which are compatible with either of the body channels simply by rotating the nail 180 degrees if switching between deployment in channels. Having an assortment of anchors to choose from allows a physician to use an anchor pair for a single body whereby the anchors are equal or unequal lengths. In an embodiment a physician may insert a relatively smaller anchor, then explant the smaller anchor, and then insert a relatively larger anchor.

The following examples pertain to further embodiments.

Example 1. An orthopedic fusion system comprising: a cage; a curved first channel coupling a lateral wall of the cage to a superior surface of the cage; a curved second channel coupling the lateral wall of the cage to an inferior surface of the cage; a third channel coupling the superior surface of the cage to the inferior surface of the cage; a curved first anchor configured to slide within the first channel; a curved second anchor configured to slide within the second channel; and a threaded projection extending outwardly from the lateral wall; a washer non-threadingly attached to the threaded projection; a cam non-threadingly attached to the threaded projection and directly contacting the washer; a nut threadingly attached to the threaded projection and directly contacting the cam.

The "superior surface" does not necessarily mean it must be the "most" superior surface or highest surface of the cage. The "inferior surface" does not necessarily mean it must be the "most" inferior surface or lowest surface of the cage.

Example 2. An orthopedic fusion system comprising: a cage; a curved first channel coupling a lateral wall of the cage to a superior surface of the cage; a curved second channel coupling the lateral wall of the cage to an inferior surface of the cage; a third channel coupling the superior surface of the cage to the inferior surface of the cage; a curved first anchor configured to slide within the first channel; a curved second anchor configured to slide within the second channel; and an insertion tool, the insertion tool comprising: a first insertion tool arm configured to travel along a first arcuate path to drive the first anchor along the first channel; a second insertion tool arm configured to travel along a second arcuate path to drive the second anchor along the second channel.

Example 3. The system of example 2 comprising: a threaded projection extending outwardly from the lateral wall; a washer non-threadingly attached to the threaded projection; a cam non-threadingly attached to the threaded projection and directly contacting the washer; a nut threadingly attached to the threaded projection and directly contacting the cam.

Example 4. The system according to any of examples 1 or 3 wherein the cam includes: a first arm that projects across a portion of the first channel in a first orientation of the cam with respect to the cage; and a second arm that projects across a portion of the second channel in the first orientation.

Example 5. The system of example 4 wherein: in a second orientation of the cam with respect to the cage: (a) the first arm does not project across the portion of the first channel; and (b) the second arm does not project across the portion of the second channel in the second orientation; the cam is rotationally linked to the threaded projection and is configured to rotate between the first and second orientations.

Example 6. The system of example 5 wherein in the first orientation a portion of the first arm is lateral to a proximal end of the first anchor and prevents the first anchor from backing out of the first channel.

Example 7. The system of example 6, wherein in a vertical plane in the first orientation the first anchor is completely surrounded by an interior wall of the first channel.

Example 8. The system of example 7 wherein the first anchor includes a projection configured to abut a wall of the first channel to prevent a proximal portion of the first anchor from passing through the first channel.

Example 9. The system of example 8 wherein the first and second insertion tool arms are configured to respectively travel along the first and second arcuate paths simultaneously with one another.

Example 10. The system of example 8 comprising a withdrawal tool, the withdrawal tool comprising a first withdrawal tool arm configured to travel along an additional first arcuate path to withdraw the first anchor from the first channel.

Example 11. The system according to any of examples 1 or 3 comprising a fourth channel coupling the lateral wall of the cage to the third channel.

Example 12. The system according to any of examples 1 or 3 comprising: a fourth channel between the first and second channels; a third anchor configured to slide within the fourth channel.

Example 13. The system according to any of examples 1 or 3 wherein a linear axis intersects the lateral wall and the first and second channels.

Example 14. The system according to any of examples 1 or 3 wherein the first anchor includes an arcuate outer wall defining an arc that extends along a majority of an overall length of the first anchor.

Example 15. The system of example 14 wherein the arc has a single consistent radius of curvature.

Example 16. The system according to any of examples 1 or 3 wherein: the cam is non-fixedly coupled to the washer; the cam is rotationally coupled to the washer.

Example 17. The system according to any of examples 1 or 3 wherein the first and second anchors are configured to deploy into the first and second channels simultaneously with one another.

Example 18. The system according to any of examples 1 or 3 wherein the nut is tightened against the cam with a predetermined level of force to force the cam against the washer.

Example 19. The system of example 1 wherein: a first plane intersects the threaded projection, the washer, the cam, and the nut but does not intersect the third channel; a second plane, orthogonal to the first plane, intersects the threaded projection, the cam, the nut, and the third channel.

Figure 1J:
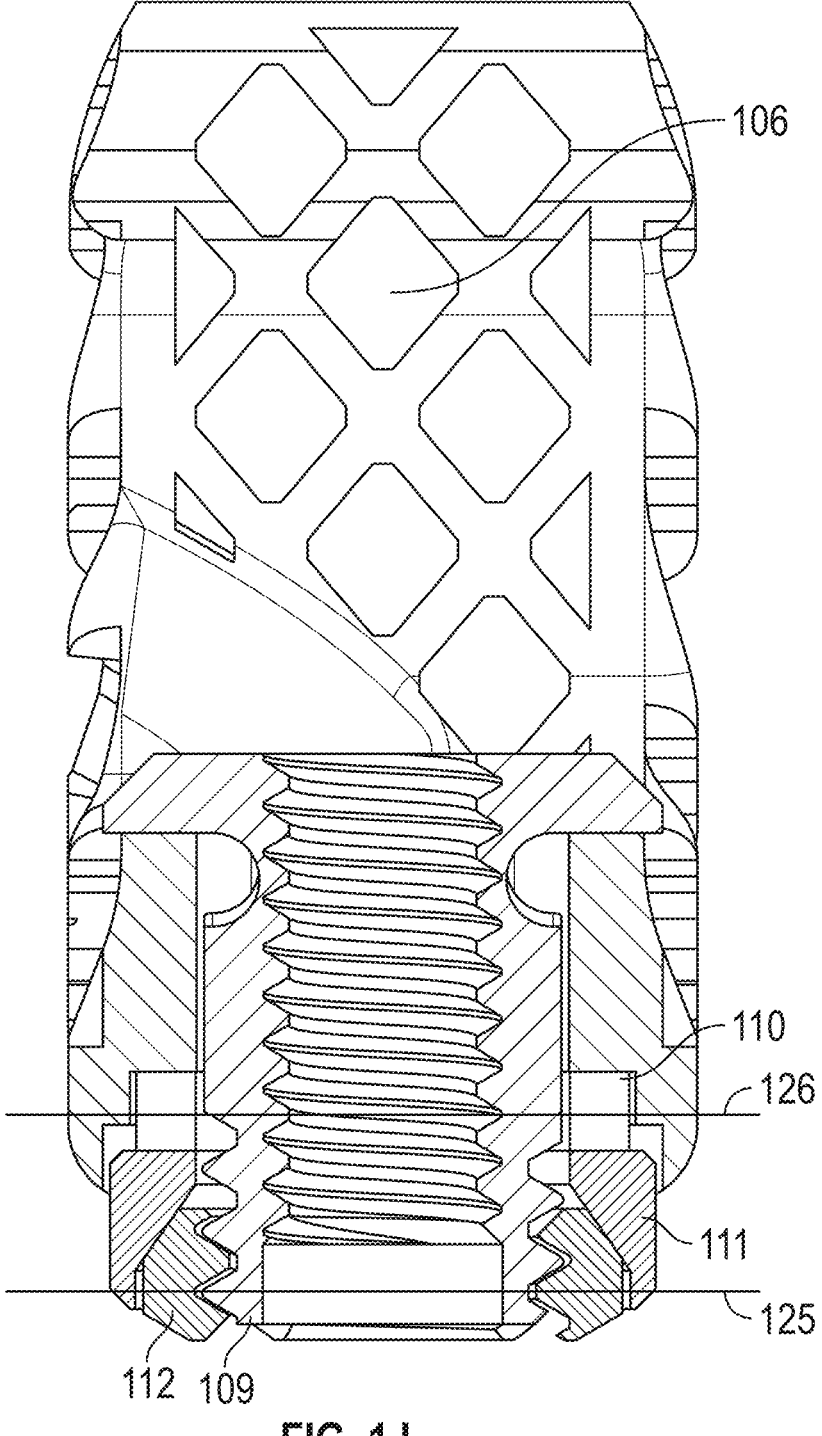
FIG. 1J includes a cross-sectional view of the embodiment of FIG. 1A.
Figure 1K:
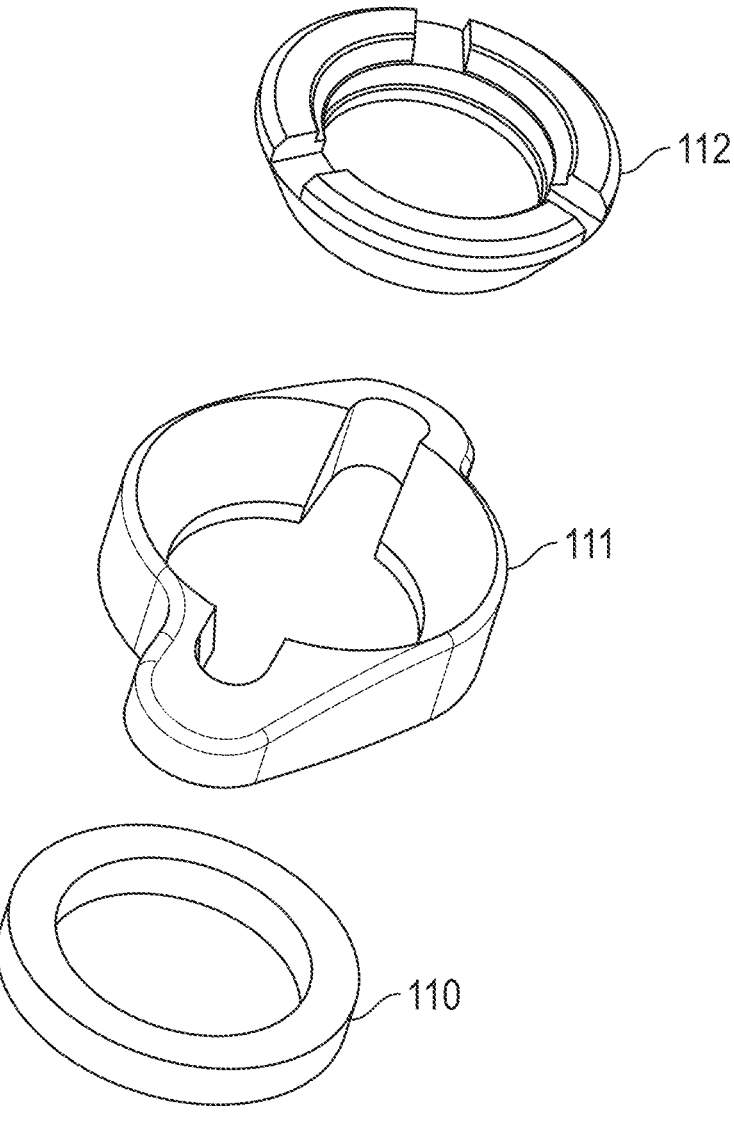
FIG. 1K includes an assembly of a portion of the cam assembly of FIG. 1A.

For example, see FIG. 1J. The cross-section is taken along the second plane and the first plane is plane 125. Additional plane 126 intersects the threaded projection and the washer but does not intersect the nut or the cam.

Example 20. The system of example 19, wherein the washer is compressed.

For example, a compressed PEEK washer provides friction to the cam to keep the cam in the open or closed position.

Example 1a. An spinal implant system comprising: a cage; a curved first channel coupling a side wall of the cage to a top surface of the cage; a curved second channel coupling the side wall of the cage to a bottom surface of the cage; a third channel coupling the top surface of the cage to the bottom surface of the cage; a threaded projection extending outwardly from the side wall; a washer non-threadingly attached to the threaded projection; a cam non-threadingly attached to the threaded projection and directly contacting the washer; a ring threadingly attached to the threaded projection and directly contacting the cam.

Thus, not all systems necessarily come with anchors. For instance, in some configurations the anchors may be provided separately from the cage. The lack of threading allows for resistance fits to maintain the cam in open/closed positions by compressing the washer.

Example 2a. The system of example 1a wherein the cam includes: a first projection that projects across a portion of the first channel in a first orientation of the cam with respect to the cage; and a second projection that projects across a portion of the second channel in the first orientation.

Example 3a. The system of example 2a wherein: in a second orientation of the cam with respect to the cage: (a) the first projection does not project across the portion of the first channel; and (b) the second projection does not project across the portion of the second channel in the second orientation; the cam is rotationally linked to the threaded projection and is to rotate between the first and second orientations.

Example 4a. The system of example 3a comprising: a curved first anchor to slide within the first channel; a curved second anchor to slide within the second channel; wherein in the first orientation a portion of the first projection is lateral to a proximal end of the first anchor and prevents the first anchor from backing out of the first channel.

Example 5a. The system of example 4a, wherein in a vertical plane in the first orientation the first anchor is completely surrounded by an interior wall of the first channel.

Example 6a. The system of example 5a wherein the first anchor includes a projection to abut a wall of the first channel to prevent a proximal portion of the first anchor from passing through the first channel.

Example 7a. The system of example 6a comprising a fourth channel coupling the side wall of the cage to the third channel.

Example 8a. The system of example 6a comprising: a fourth channel between the first and second channels; a third anchor to slide within the fourth channel.

Example 9a. The system of example 6a wherein a linear axis intersects the side wall and the first and second channels.

Example 10a. The system of example 6a wherein the first anchor includes an arcuate outer wall defining an arc that extends along a majority of an overall length of the first anchor.

Example 11a. The system of example 10a wherein the arc has a single consistent radius of curvature.

Example 12a. The system of example 11a wherein the first and second anchors have identical forms to each other.

For instance, each anchor may be used in either of the first or second channels.

Example 13a. The system of example 12a wherein the cam is unthreaded.

Example 14a. The system of example 13a wherein: the cam is non-fixedly coupled to the washer; the cam is rotationally coupled to the washer.

Example 15a. The system of example 14a wherein: a first plane intersects the threaded projection, the washer, the cam, and the ring; the first plane does not intersect the third channel; a second plane, orthogonal to the first plane, intersects the threaded projection, the washer, the cam, the ring, and the third channel.

Example 16a. The system of example 15a, wherein the washer is compressed.

Example 17a. The system of example 16a wherein the ring is tightened against the cam with a predetermined level of force to force the cam against the washer.

Example 18a. The system of example 16a wherein the washer includes polyetheretherketone (PEEK).

Example 19a. The system of example 1a comprising an insertion tool, the insertion tool comprising: a first insertion tool projection to travel along a first arcuate path to drive the first anchor along the first channel; a second insertion tool projection to travel along a second arcuate path to drive the second anchor along the second channel.

Example 20a. The system of example 19a wherein the first and second insertion tool arms are configured to respectively travel along the first and second arcuate paths simultaneously with one another.

The foregoing description of the embodiments of the invention has been presented for the purposes of illustration and description. It is not intended to be exhaustive or to limit the invention to the precise forms disclosed. This description may include terms, such as left, right, top, bottom, over, under, upper, lower, first, second, etc. that are used for descriptive purposes only and are not to be construed as limiting. For example, terms designating relative vertical position refer to a situation where a side of a device is the "top" surface of that device; however the device may actually be in any orientation so that a "top" side of a device may be lower than the "bottom" side in a standard terrestrial frame of reference and still fall within the meaning of the term "top." Persons skilled in the art will recognize various equivalent combinations and substitutions for various components shown in the Figures. It is therefore intended that the scope of the invention be limited not by this detailed description.

What is claimed is:

1. An spinal implant system comprising:
a cage;
a curved first channel coupling a lateral wall of the cage to a superior surface of the cage;
a curved second channel coupling the lateral wall of the cage to an inferior surface of the cage;
a third channel coupling the superior surface of the cage to the inferior surface of the cage;
a curved first anchor configured to slide within the first channel;
a curved second anchor configured to slide within the second channel; and
a threaded projection extending outwardly from the lateral wall;
a washer non-threadingly attached to the threaded projection;
a cam non-threadingly attached to the threaded projection and directly contacting the washer;
a nut threadingly attached to the threaded projection and directly contacting the cam.

2. The system of claim 1 wherein the cam includes:
a first arm that projects across a portion of the first channel in a first orientation of the cam with respect to the cage; and
a second arm that projects across a portion of the second channel in the first orientation.

3. The system of claim 2 wherein:
in a second orientation of the cam with respect to the cage: (a) the first arm does not project across the portion of the first channel; and (b) the second arm does not project across the portion of the second channel in the second orientation;
the cam is rotationally linked to the threaded projection and is configured to rotate between the first and second orientations.

4. The system of claim 3 wherein in the first orientation a portion of the first arm is lateral to a proximal end of the first anchor and prevents the first anchor from backing out of the first channel.

5. The system of claim 4, wherein in a vertical plane in the first orientation the first anchor is completely surrounded by an interior wall of the first channel.

6. The system of claim 5 wherein the first anchor includes a projection configured to abut a wall of the first channel to prevent a proximal portion of the first anchor from passing through the first channel.

7. The system of claim 6 comprising a fourth channel coupling the lateral wall of the cage to the third channel.

8. The system of claim 6 comprising a fourth channel between the first and second channels.

9. The system of claim 6 wherein a linear axis intersects the lateral wall and the first and second channels.

10. The system of claim 6 wherein the first anchor includes an arcuate outer wall defining an arc that extends along a majority of an overall length of the first anchor.

11. The system of claim 10 wherein the arc has a single consistent radius of curvature.

12. The system of claim 11 wherein the first and second anchors have identical forms to each other.

13. The system of claim 12 wherein the cam is unthreaded.

14. The system of claim 13 wherein:
the cam is non-fixedly coupled to the washer;
the cam is rotationally coupled to the washer.

15. The system of claim 14 wherein:
a first plane intersects the threaded projection, the cam, and the nut;
the first plane does not intersect the third channel;
a second plane, orthogonal to the first plane, intersects the threaded projection, the washer, the cam, the nut, and the third channel.

16. The system of claim 15, wherein the washer is compressed.

17. The system of claim 16 wherein the nut is tightened against the cam with a predetermined level of force to force the cam against the washer.

18. The system of claim 16 wherein the washer includes polyetheretherketone (PEEK).

19. The system of claim 1 comprising an insertion tool, the insertion tool comprising:
a first insertion tool arm configured to travel along a first arcuate path to drive the first anchor along the first channel;
a second insertion tool arm configured to travel along a second arcuate path to drive the second anchor along the second channel.

20. The system of claim 19 wherein the first and second insertion tool arms are configured to respectively travel along the first and second arcuate paths simultaneously with one another.

\* \* \* \* \*